United States Patent [19]
Adair

[11] Patent Number: 5,873,814
[45] Date of Patent: *Feb. 23, 1999

[54] STERILE ENCAPSULATED ENDOSCOPIC VIDEO MONITOR AND METHOD

[76] Inventor: Edwin L. Adair, 317 Paragon Way, Castle Pines Village, Colo. 80104

[*] Notice: The term of this patent shall not extend beyond the expiration date of Pat. No. 5,812,188.

[21] Appl. No.: 867,343

[22] Filed: Jun. 2, 1997

Related U.S. Application Data

[63] Continuation-in-part of Ser. No. 678,811, Jul. 12, 1996, Pat. No. 5,812,188.

[51] Int. Cl.$^6$ .................................................. A61B 1/04
[52] U.S. Cl. ........................... 600/109; 600/131; 348/65
[58] Field of Search .................................... 600/101, 113, 600/131, 109, 160, 112; 348/65, 71, 72, 74

[56] References Cited

U.S. PATENT DOCUMENTS

| | | |
|---|---|---|
| 1,535,312 | 4/1925 | Hosking . |
| 3,162,107 | 12/1964 | Byers . |
| 3,929,178 | 12/1975 | Hickey . |
| 4,155,453 | 5/1979 | Ono . |
| 4,275,719 | 6/1981 | Mayer . |
| 4,604,992 | 8/1986 | Sato ......................................... 600/109 |
| 4,621,735 | 11/1986 | Coon et al. . |
| 4,633,304 | 12/1986 | Nagasaki ................................. 600/109 |
| 4,654,701 | 3/1987 | Yabe ........................................ 600/118 |
| 4,742,819 | 5/1988 | George . |
| 4,879,992 | 11/1989 | Nishigaki et al. ....................... 600/110 |
| 4,963,693 | 10/1990 | Kodl . |
| 5,020,546 | 6/1991 | Russo . |
| 5,080,155 | 1/1992 | Crozier . |
| 5,316,541 | 5/1994 | Fischer . |
| 5,332,095 | 7/1994 | Wu . |
| 5,363,838 | 11/1994 | George . |
| 5,429,142 | 7/1995 | Szabo et al. . |

FOREIGN PATENT DOCUMENTS

| | | | |
|---|---|---|---|
| 9315648 | 8/1993 | WIPO | ..................................... 600/112 |

OTHER PUBLICATIONS

Sharp Corporation, *Color Display Modules,* Jan., 1995, pp. 1–13.
Sony Corporation, *8.6" LCD Monitor Module, SEU–2092,* pp. 1–2.
Sony Corporation, *10.4" LCD Monitor Module, LMD–1040XC,* pp. 1–2.
Laser Focus World, *Display Technology Helps to Tell a Story,* May, 1997.
Advanced Imaging, "Clear Imaging for Untethered Communication: Hopin's Sharp, Tiny LCD CyberDisplay", p. 53, May, 1997.
Sales Brochure *EndoView and EndoSpeak.*
Olympus Corporation Product Brochure *Perspectives in Endoscopy,* Issue No. 2, 1992.

*Primary Examiner*—John P. Leubecker
*Attorney, Agent, or Firm*—Fields and Johnson, P.C.

[57] ABSTRACT

A sterile enclosure is provided having a body portion for encapsulating one or more monitor modules used for viewing one or more surgical areas in a sterile operating field. The video monitor can be very thin and lightweight monitor modules. The sterile enclosure may be flexible or rigid and have one or more cable drapes extending from the body to cover one or more cables associated with the video monitor. In some embodiments, the body is flexible. In another embodiment, the body is rigid. The body is transparent in at least an area for viewing the screen of the video monitor and is substantially impervious to liquid and gas. A vacuum line may be connected to the body portion to evacuate air therefrom. The video monitor may be controlled by controls located on the monitor, or may be controlled by voice activation or by a remote video control system. During use, the monitor module may be placed on or adjacent to the patient. Alternatively, a miniaturized sterile monitor module or LCD display unit may be provided which is directly mountable to a surgical instrument such as an endoscope.

18 Claims, 10 Drawing Sheets

Fig_18

Fig_17

Fig_19

STERILE ENCAPSULATED ENDOSCOPIC VIDEO MONITOR AND METHOD

TECHNICAL FIELD

This application is a continuation in part of U.S. Ser. No. 08/678,811 filed on Jul. 12, 1996, and entitled "Sterile Encapsulated Endoscopic Video Monitor and Method", now U.S. Pat. No. 5,812,188.

This invention relates to an apparatus and method which provides a visual display of a surgical site and more particularly to a sterile encapsulated endoscopic video monitor and method used in conjunction with an endoscopic camera and instrument to provide an image of a surgical area within the sterile field of a surgical area.

BACKGROUND ART

Endoscopic procedures have become the standard in modern medicine for conducting surgical procedures which are minimally invasive. Prior to the development of endoscopic procedures, surgery required direct visual access to the surgical area which oftentimes resulted in extreme trauma to the patient due to large incisions and the like. With the development of endoscopic instruments which include video cameras that can transmit an image of the surgical site to a video display, surgical procedures can be conducted in a less invasive manner. Although endoscopic procedures represent a great leap forward in terms of minimizing patient trauma, endoscopic procedures using video displays have also resulted in new problems.

One prerequisite for successful endoscopic procedures is that the surgeon must be skilled with the use of the endoscope so that the endoscope and associated endoscopic operative instruments do not cause unnecessary damage to the patient's tissues. In most endoscopic procedures conducted today, the surgeon may view a standard television (TV) monitor or video screen which displays an image of the surgical site as photographed by a video camera positioned within or adjacent the endoscopic instrument. One problem created by the use of endoscopes with integral video cameras is that the surgeon must be able to precisely manipulate the endoscope within the patient's body while looking away from the patient and toward the remote TV monitor. Since the standard TV monitor must be placed at a location substantially remote from the patient's body, surgeons have had to develop particular dexterity and skill in ensuring that the endoscope does not unintentionally damage body tissues during the surgical procedure.

Another problem associated with endoscopic procedures utilizing TV monitors or video screens is that the surgeon is dependent upon another person to control the exact type of image displayed on the TV monitor. More particularly, the surgeon may be able to adjust the focus of the image by a dial located upon the endoscope; however, neither the endoscope nor the camera attached to the endoscope have controls to vary the brightness, contrast or magnification of the image. Accordingly, the surgeon must direct operating room personnel to adjust the visual display as desired.

Another problem associated with the advent of endoscopic procedures utilizing video equipment is that since additional equipment is brought into the operating room, there is a concern for preventing contamination by the equipment of the sterile field of the operating room. Since TV monitors and other electronic equipment tend to naturally induce or create an electric charge, microbes clinging to dust particles tend to collect on this equipment wherein such microbes can then be transmitted to the sterile operating field of the operating room. It has been found that a surgeon placing his hand near a TV monitor displaying an image of the surgical area can attract undesirable microbes via the differential in electrostatic charge between the surgeon's hand and the TV or monitor screen.

Additionally, standard TV monitors and their associated controls are typically large and heavy and difficult to manipulate within the operating room. Accordingly, this equipment cannot be placed directly adjacent to or on the patient to enhance the surgeon's ability to manipulate the endoscopic instrument in a visually aligned position.

Each of the above-identified disadvantages of current endoscopic procedures utilizing standard video equipment is overcome by the invention claimed herein.

DISCLOSURE OF THE INVENTION

According to the present invention, a sterile encapsulated endoscopic video monitor and method are provided. According to the first embodiment of the invention, a sterile enclosure is provided for encapsulating a video monitor or monitor module. As used herein, the term "video monitor" refers to all devices which can provide a visual image to include standard TV monitors, standard computer or laptop computer monitors, monitor modules which are much lighter in weight than TV monitors and which have much smaller profiles in terms of depth or thickness, and tiny LCD display units which are even smaller than a monitor module and can still provide a high quality visual image.

Examples of monitor modules available are those manufactured by Sony, known as "LCD Monitor Modules," which have particularly thin bodies and are lightweight. For example, Model No. SCU-2092, manufactured by Sony, is a chassis-type LCD monitor module having a 58 mm depth and weighing less 2,000 grams. In addition to Sony, there are manufacturers of similar monitor modules in terms of weight and depth or thickness such as Texas Instruments, Xerox, Sharp, Polaris Video and Epson. Additionally, these monitors have a high degree of resolution which match the resolution currently found in standard high resolution monitors known in the art as "SVGA" monitors. One company manufacturing such a high resolution monitor is Pixtech of Santa Clara, Calif. Each of these monitor modules are self-contained units in that the monitor modules require, at most, a single communication cable, which communicates with a video camera system and a power source. Some manufacturers make monitor modules which require no communication or power cables and communicate with a video camera system by means of infrared, radio or other known electromagnetic signals. Also, these monitor modules may be powered by their own internal power source. Thus, it shall be understood that the monitor modules described herein do not necessarily require any communication cables or power cables in order to produce an image of the surgical site.

One company which manufacturers a high quality LCD display unit is Kopin Corporation of Taunton, Md. One model offered by Kopin Corporation is a product called the "Cyber Display 320." This product is an active matrix liquid crystal display (AMLCD) unit having an extremely high density of 1,700 lines of information per inch. This particular AMLCD is only 0.24 inches as measured from the diagonal. It further has 76,800 individual pixels for the presentation of text, graphics or video. The monochrome version has more than 256 levels of gray which provides exceptional contrast for the image.

The sterile enclosure includes a flexible body which is adaptable to receive video monitors or monitor modules of varying shapes and sizes. The open proximal end of the sterile enclosure may be sealed for completely enclosing the monitor module therein. One or more ports may be formed on the flexible body of the sterile enclosure enabling cables or other communication structures to exit the sterile enclosure for communication with other video equipment within the operating room. The sterile enclosure may be made of a homogeneous material which is substantially transparent so that the monitor screen of the monitor module may be easily viewed during a surgical procedure in a sterile encapsulated state. Alternatively, a separate, highly transparent window portion may be formed on the sterile enclosure which is made of a different material than the flexible body portion and which enhances the ability to view the monitor screen of the monitor module. For example, the sterile enclosure may be made of styrene or polyethylene and the window portion may be made of acrylic or polycarbonate. The sterile enclosure is substantially liquid and gas impermeable to prevent contaminants within the encapsulated monitor module from migrating into the sterile field of the surgical area.

A corresponding cable drape may be provided at each of the ports to ensure that any cables which may exit the sterile enclosure are isolated from the sterile field of the surgical area. Alternatively, the cables exiting the sterile enclosure may be completely sealed units within themselves such that no cable drape is necessary. That is, the cables may be attached directly to the monitor module via a watertight connector integral with the cable ends. Furthermore, the actual cable structures themselves may be completely waterproof. Examples of such waterproof connectors and cables are those manufactured by Fisher Connectors of Valencia, Calif. Such connectors and cables may also be disinfected and/or sterilized by soaking them in a disinfecting solution, or sterilization by exposure to a gas sterilization procedure utilizing ethylene oxide or the like.

A vacuum port may be formed on the flexible body of the sterile enclosure and connected to a source of vacuum external to the monitor module. The vacuum source may be used to pull a vacuum on the interior open space within the sterile enclosure which covers the monitor module and associated cable(s).

In another embodiment, the sterile endoscopic encapsulated video monitor of this invention may include a rigid or semi-rigid monitor module frame which encloses the video monitor or monitor module therein. The monitor module frame may be a unitary piece formed by injection molding, or the monitor module frame may be constructed of two pieces of material that join together at a sealed interface. A sealing material such as acrylic or the like may then completely cover the monitor module frame and the exposed monitor screen of the monitor module. Accordingly, the sealing material provides a gas and liquid impervious encasement for the monitor module held within the monitor module frame. In one variation of this embodiment, the monitor module frame itself may be gas and liquid impervious and include an integral transparent cover forming a window portion that is positioned over the monitor screen of the monitor module. In this variation, no sealing material is required because the monitor module frame and transparent cover completely encapsulates the monitor module therein. A cable drape may be sealed to the monitor module frame enabling communication cables and the like to exit the sealed monitor module. Alternatively, waterproof cables and connectors may be used.

As with the waterproof cables and connectors, the monitor module frame itself may be sterilized by soaking it in a disinfecting solution or may be gas sterilized. Since the monitor module frame may be completely sterilized, a monitor module housed within the monitor module frame may be used a number of times without having to place the monitor module in a new monitor module frame. This sterilizable feature of the monitor module housed within the monitor module frame greatly enhances the ease in which a visual display of a surgical area can be provided within close proximity of the surgeon. Accordingly, no separate sterile enclosure is required since the sealed monitor module frame is sterilizable as a stand-alone unit.

In another embodiment, a standard laptop computer may be used in conjunction with the sterile enclosure. In this embodiment, separate ports are formed on the flexible body of the sterile enclosure for enabling a vacuum to be pulled on the interior open space of the sterile enclosure covering the laptop computer and another port for handling any cables which may communicate with other video equipment within the surgical area.

In yet another embodiment, at least two or more video monitors may be housed within a single sterile enclosure which allows a surgeon to view a number of surgical sites simultaneously or to view the same surgical site from a number of different viewpoints. Some surgical procedures may require a surgeon to have more than one view of a particular surgical area. In other circumstances, a surgeon may be conducting surgical procedures on remote locations of the patient's body. In either case, the ability for a surgeon to view separate surgical sites or the same surgical site from different viewpoints can greatly increase the safety and efficiency of the overall surgical procedure. Accordingly, this embodiment provides a sterile enclosure having a plurality of transparent covers formed on the single sterile enclosure. The screen of each video monitor may be viewed through the transparent covers.

Depending upon the type of video monitor used, a surgeon may manipulate the image shown on the monitor screen by either touch screen controls which are activated by touching the monitor screen or by a plurality of membrane switches which are separately formed on the monitor module frame and wired so that they may control the image shown on the video monitor.

As for the first and second embodiments, again depending upon the type of video monitor used, control of the image shown on the monitor screen may be achieved either by touch screen features or by membrane switches or keypads which are manufactured as part of the video monitor or monitor module.

The video monitor of this invention may also be accompanied with other features to assist a surgeon in manipulation of the image or in recording data represented by the image. For example, the images may be stored in a CD-ROM format or may be printed on a video printer which communicates with the monitor module. Additionally, the touch screen features of the monitor module may allow a surgeon to access software programs which may interpret or provide information relating to the images shown on the monitor screen. Also, in lieu of any physical contact by the surgeon with the video monitor, it may be controlled by voice activation. That is, the video monitor or the monitor module frame may be equipped with a wireless or wired speaker and microphone and which communicate by the desired electromagnetic means (for example, radio waves) with the video or control system or computer which can be used to control the images displayed on the monitor screen. One commercial example of a turnkey system which incorporates voice activation and accompanying software for manipulating and recording data are products called Endoview™ and Endospeak® manufactured by CompuSpeak Laboratories, Inc. of Olathe, Kans.

In operation, the sealed video monitor may be placed directly on the patient or directly adjacent to the patient at a location in which surgery is being performed. By the use of lightweight and compact monitor modules which can be easily maintained in a sterile state by use of the sterile enclosure or sealing material, a video image of the surgical area can be provided to a surgeon in an aligned position with respect to the surgical area. This position can be along the surgeon's normal line of vision to minimize fatigue and discomfort.

In lieu of placing the video monitor directly on or adjacent the patient, a miniaturized monitor module may be attached directly to the endoscopic instrument used in performing the surgical procedure. As further explained below, the video monitor of this invention may be attached to endoscopes of the types described in my earlier U.S. Pat. Nos. 5,402,768, 5,498,230, or 5,489,256. The disclosure of these references are hereby incorporated by reference.

It may be desirable to use a LCD display unit in conjunction with the endoscope. The LCD display unit may be formed integrally with the outer sheath or wall of the endoscope. Accordingly, this LCD display unit may be sterilized with the endoscope as a single unit. The portion of the LCD display unit which may protrude outwardly from the endoscope may be coated with an appropriate material such as acrylic which enables the LCD display unit to be completely sealed with respect to the endoscope.

Additional advantages of this invention will become apparent from the description that follows, taken in conjunction with the accompanying drawings.

BRIEF DESCRIPTION OF THE DRAWINGS

FIG. 12 is a fragmentary vertical section and side view of a monitor module mounted directly to an endoscope of the type described in my earlier U.S. Pat. No. 5,498,230;

FIG. 13 is a partially exploded perspective view of a monitor module engageable with the endoscope described in FIG. 12;

FIG. 14 is another perspective of the endoscope described in FIG. 12, the endoscope including a LCD display unit in lieu of a monitor module;

BEST MODE FOR CARRYING OUT THE INVENTION

Figure 1:
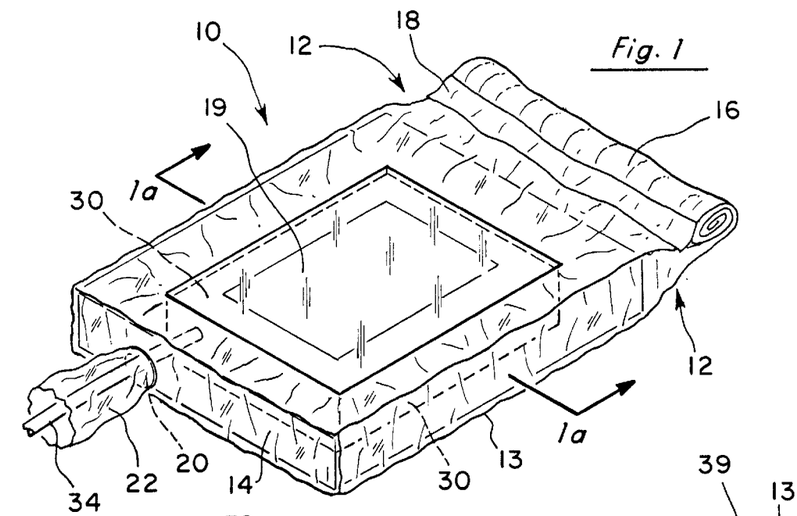
FIG. 1 is a perspective view of a first embodiment of the sterile encapsulated endoscopic video monitor of this invention.
Figure 1A:
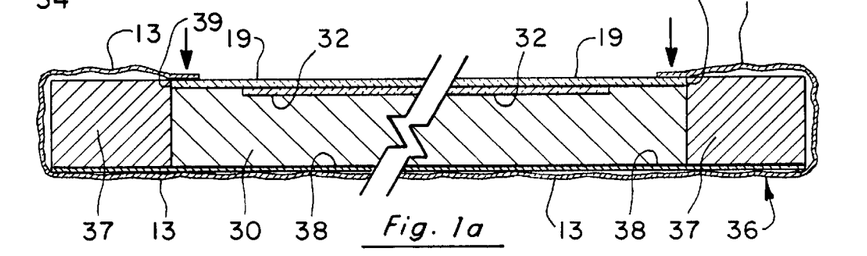
FIG. 1a is a fragmentary enlarged vertical section, taken along line 1a of FIG. 1, illustrating the positioning of a monitor module mounted in one type of monitor module frame and covered by a sterile enclosure.
Figure 2:
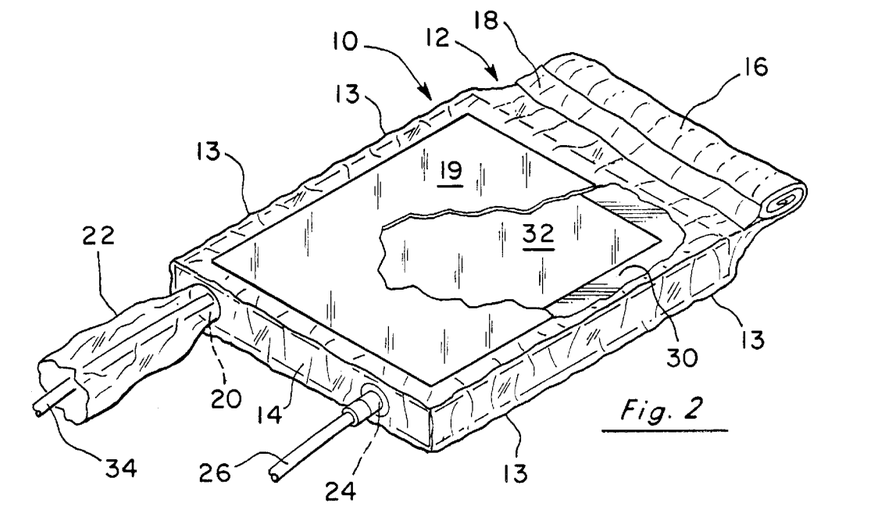
FIG. 2 is a fragmentary perspective view, similar to FIG. 1, showing a sterile enclosure having a transparent cover defining a window portion adapted to correspond with a particular type of monitor module.

According to the first embodiment as shown in FIGS. 1, 1a and 2, the sterile encapsulated endoscopic video monitor of this invention 10 includes a video monitor or monitor module 30 which is placed inside a sterile enclosure 12. The sterile enclosure 12 includes a flexible body 13 which may conform to the particular shape of the monitor module used. The sterile enclosure 12 is defined by a closed distal end 14 and an open proximal end 16 which receives a monitor module 30. An enclosure seal 18 lies adjacent the proximal end 16 to completely seal the monitor module 30 inside the sterile enclosure 12 thus isolating the monitor module 30 from the sterile field of the surgical area. Enclosure seal 18 may be adhesive tape or another appropriate sealing means. In general, the sterile field of the surgical area or operating room is situated around the body of the patient P. The sterile enclosure 12 may be made of a substantially transparent and liquid and gas impermeable material such as polyurethane, polyolefins, polyethylene, polystyrene, laminated plastic films or the like. Optionally, an integral transparent cover defining a window portion 19 may be formed along a cut-out or laminated portion of the flexible body 13 so that the window portion enhances the ability to view the monitor screen within the sterile enclosure 12. The window portion 19 may be made of an optically clear material such as acrylic or polycarbonate and, if desired, may be more rigid than enclosure 12. The window portion 19 is completely sealed with respect to the flexible body 13 so that contamination cannot exit the interior open space within the sterile enclosure 12 into the sterile field. A cable port 20 may be formed on the distal end 14 of the sterile enclosure 12 to accommodate the exit of communication and/or power cables such as cable 34 which connects to the monitor module 30. Accordingly, a cable drape 22 may be provided to completely seal cable 34 from the sterile field. As shown in FIG. 1a, the monitor module 30 includes a monitor screen 32 which is positioned adjacent the window portion 19. Additionally, window portion 19 may be sized to fit the particular type of monitor screen 32 of the monitor module 30.

As shown in FIG. 2, a vacuum port 24 may be provided on the sterile enclosure 12 and placed in communication with a vacuum line 26 connected to an external source of vacuum (not shown) so that the sterile enclosure may be tightly held against the monitor module 30. By drawing a vacuum upon the interior open space within the sterile enclosure 12, distortion of an image may be minimized by undulations or folds in the window portion 19. Additionally, the sterile enclosure 12 is less likely to be torn or ripped if held tightly against the monitor module. Depending upon how the monitor module 30 is to be supported on or adjacent to a patient, the enclosure 12 may also encapsulate a support structure (not shown) which may support the monitor module above or adjacent the patient. Accordingly, the support structure in addition to the monitor module are made sterile.

As shown in FIG. 1a, a first type of monitor module frame 36 may be provided to help stabilize the monitor module 30 within the sterile enclosure 12. Oftentimes, a monitor module 30 may have a particularly sharp edge which, if exposed, may inadvertently rip or tear the sterile enclosure 12. As shown, the monitor module frame 36 may include an upper peripheral portion 37 extending around the peripheral edges of the monitor module 30 and a lower portion 38 which covers the back side of the monitor module. The window portion 19 may be held centered over the monitor screen 32 by pressing the outside edges of the window portion 19 against protruding interior edges 39 of upper portion 37.

FIG. 2 illustrates a monitor module which does not have sharp edges that could present a danger of ripping or puncturing the sterile enclosure 12 and which is placed directly in a sterile enclosure without a monitor module frame. In this embodiment, the window portion 19 simply lies over the screen 32; the window portion 19 being large enough that shifting of the monitor module 30 inside the sterile enclosure will still allow viewing of the screen 32 through window portion 19.

Figure 3:
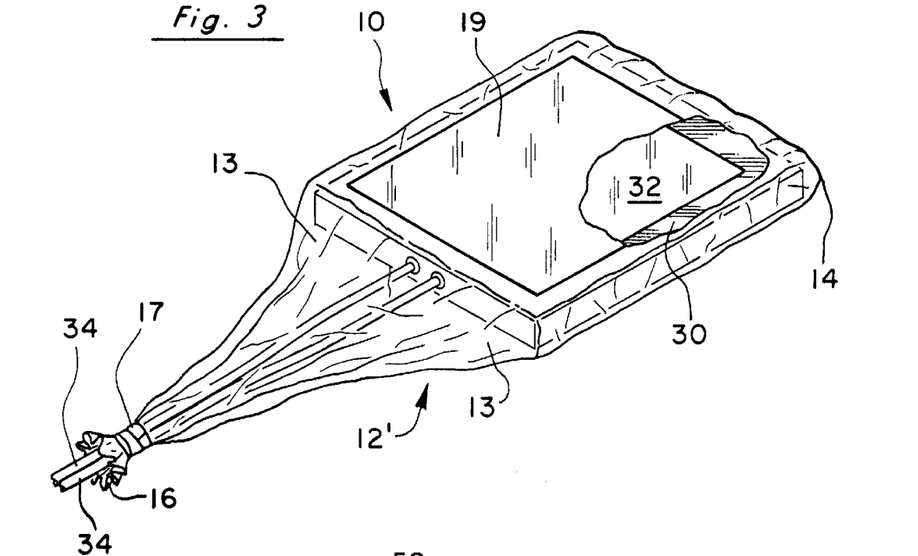
FIG. 3 is a fragmentary perspective view, similar to FIGS. 1 and 2, illustrating a modified sterile enclosure having a transparent cover defining a window portion adapted to correspond to a particular type of monitor module.

As illustrated in FIG. 3, a modified sterile enclosure 12' is provided for encapsulating a monitor module 30 and its associated cables 34 therein. As shown, the modified sterile enclosure 12' may simply include a closed distal end 14 and an open proximal end 16 in which the monitor module 30 and cables 34 are inserted. Adhesive tape or a tie structure 17 may be provided to isolate the cables 34 and module 30 from the surrounding environment. Thus, in this modified sterile enclosure 12', a separate cable drape 22 is eliminated. As with the sterile enclosure shown in FIG. 2, the modified sterile enclosure 12' shown in FIG. 3 may also be equipped with a vacuum port 24 for connection with a source of vacuum (not shown) in order to draw a vacuum on the sterile enclosure.

Figures 4, 4A:
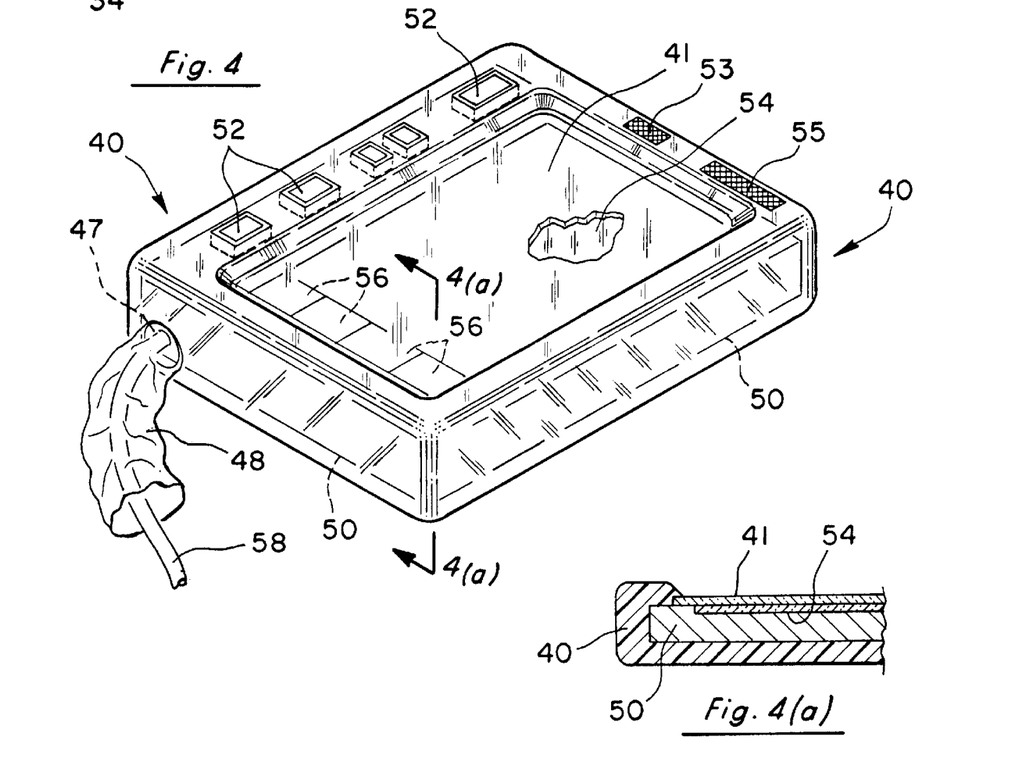
FIG. 4 is a perspective view of a second embodiment of the sterile encapsulated endoscopic video monitor and method of this invention illustrating a monitor module mounted within another type of a monitor module frame which is made as a sterilizable unitary piece with membrane switches located thereon.
FIG. 4a is a fragmentary vertical section, taken along line 4a of FIG. 4, illustrating the relationship of the monitor module housed within the sterilizable monitor module frame.

According to a second embodiment of the sterile encapsulated endoscopic video monitor of this invention, as shown in FIGS. 4 and 4a, a sterilizable, unitary and completely sealed monitor module frame 40 is provided for housing a video monitor or monitor module 50 therein. This modified frame 40 includes a transparent cover defining an integral window portion 41 which is aligned with the monitor screen 54 of the monitor module 50. Monitor module 50 is encapsulated within the frame 40 during the formation of frame 40 which is achieved, for example, by injection molding then attaching and sealing the window portion 41 thereto.

Figures 5, 5A:
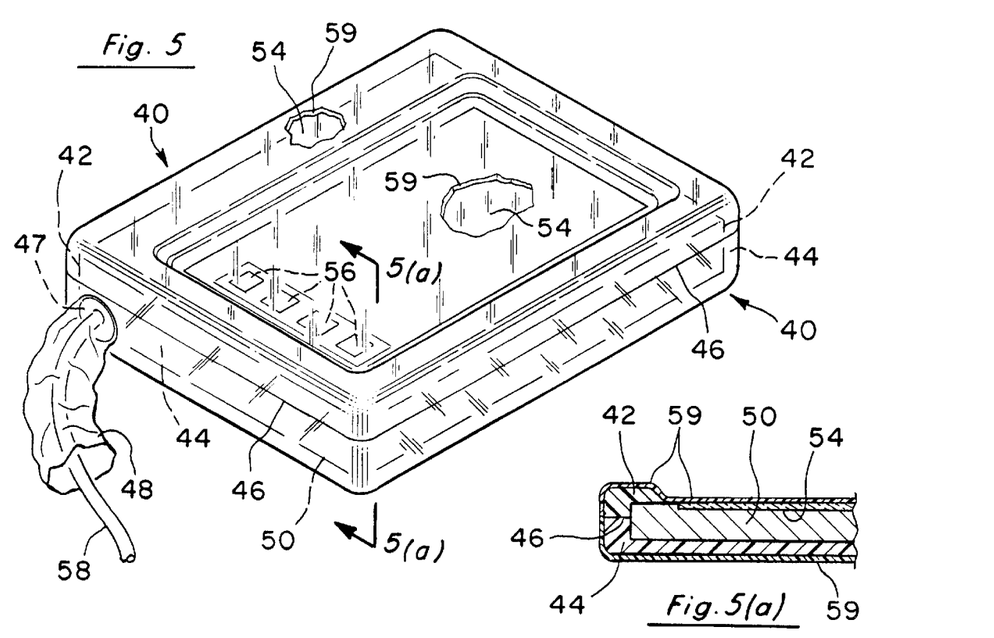
FIG. 5 is another perspective view of the second embodiment of this invention illustrating the sterilizable monitor module frame of two-piece construction with touch screen controls located on the monitor screen of the monitor module which can be activated through a sealing material covering the monitor module frame.
FIG. 5a is a fragmentary vertical section, taken along line 5a of FIG. 5, illustrating the relationship of the monitor module housed within the monitor module frame and encapsulated in the sealing material.

According to one variation of the second embodiment, as shown in FIG. 5, a clamshell type monitor module frame 40 includes an upper portion 42 and a lower portion 44 which houses the monitor module 50 therein. A sealed interface 46 defines the connection of the upper portion 42 to the lower portion 44. As best seen in FIG. 5a, monitor module 50 is completely encapsulated within a sealing material 59 such as acrylic so that the monitor module is isolated from the sterile field of the surgical area. As shown, the upper portion 42 of the monitor module frame 40 has an opening which corresponds in size and shape to the monitor screen 54. Conveniently, the sealing material 59 directly contacts the monitor screen 54 and is transparent at least over the opening to permit viewing of the monitor screen 54.

Referring back to FIG. 4, external membranes switches 52 may be positioned on the monitor module frame 40. These switches may be wired with the controls of the monitor module to directly control the visual images displayed on the monitor screen 54. FIG. 4 also illustrates the use of speaker 53 and a microphone 55 which may be formed directly on the monitor module frame 40. The speaker and microphone include corresponding communication cables (not shown) which may connect to the electronics of the monitor module which, in turn, connect to a video control device or computer, or such cables may traverse within the frame 40 and outwardly through the cable drape 48 in order to communicate directly with the computer or video control device. The microphone enables voice activation control of the functions of the monitor module to include data recording. The speaker may provide audio signals back to the surgeon such as certain status conditions of the images shown on the monitor screen, or other signals such as when data is being recorded and the like.

Alternatively, as shown in FIG. 5, touch screen switches 56 may be utilized so that control of an image on the monitor screen 54 is achieved by simply touching the sealing material 59 with a finger or a light pen at the appropriate location. As shown in both FIGS. 4 and 5, the monitor module may include a monitor module cable 58 which must also be isolated from the sterile field. Accordingly, a cable port 47 allows the cable 58 to exit the monitor module frame and is completely covered by cable drape 48 which is sealed against the monitor module frame 40.

Although the aforementioned embodiments illustrate monitor modules including exiting cables, monitor modules are manufactured which do not require any cables for power or communication and can communicate with a video or camera system or other peripherals via infrared, radio or other electromagnetic means.

Figure 6:
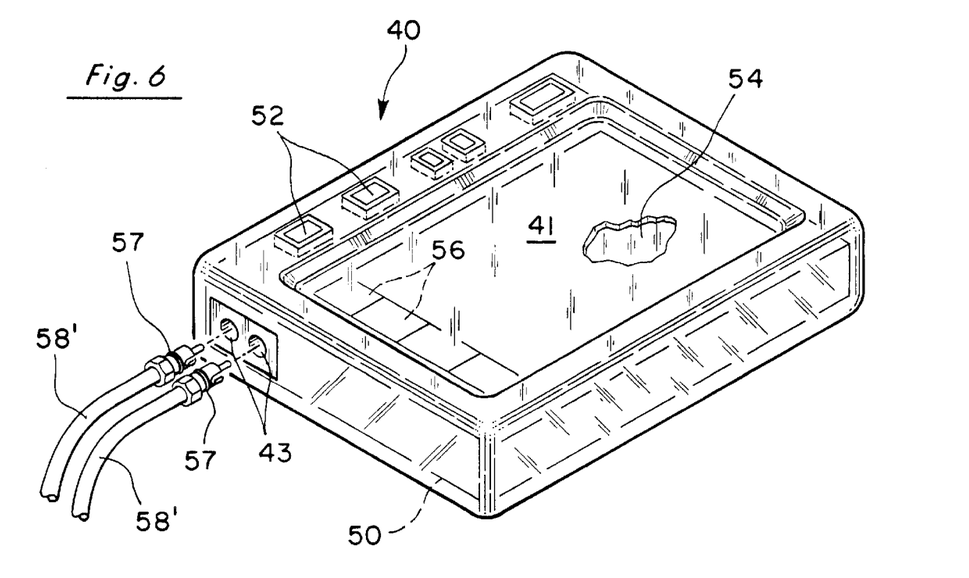
FIG. 6 is another perspective view of the second embodiment of this invention illustrating the monitor module frame as a unitary piece with membrane switches located thereon and further including waterproof cables and connectors engageable with the sterilizable monitor module frame.

FIG. 6 shows yet another preferred arrangement of cables which may need to communicate with the monitor module. As illustrated, waterproof cables 58' with integral waterproof connectors 57 may attach to ports 43 formed on the monitor module frame 40. By use of waterproof connectors 57 and waterproof cables 58', a cable drape 48 is unnecessary for providing a waterproof seal between the monitor module frame 40 and any exiting cables. As discussed above, providing a monitor module within a completely sealed monitor module frame eliminates the need for a separate sterile enclosure for use of the monitor module within the sterile field of an surgical area. The sealing material 59 may be of the type which is most advantageously sterilized through immersion in a disinfectant solution, a gas sterilization or other procedures known in the art. For example, depending upon the type of waterproof connectors and waterproof cables used, a sterilization protocol could be chosen in which the monitor module frame housing the monitor module was sterilized simultaneously in the same sterilization protocol that sterilizes the corresponding waterproof cables and connectors.

Figure 7:
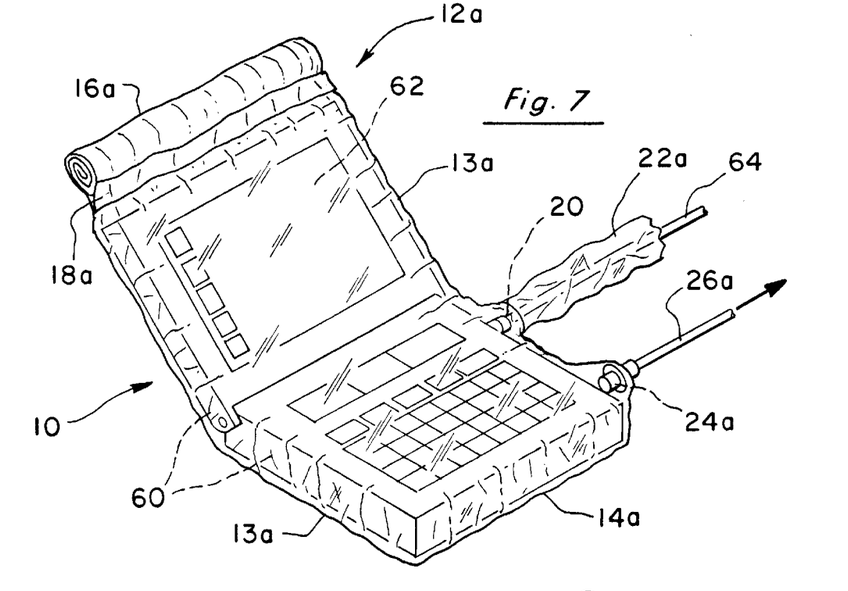
FIG. 7 is a perspective view of a third embodiment of the sterile encapsulated endoscopic video monitor of this invention illustrating a standard laptop computer sealed within a sterile enclosure.

As shown in FIG. 7, in a third embodiment, the encapsulated video monitor of this invention may be in the form of a standard laptop computer 60 that is encapsulated within a sterile enclosure 12a similar to the sterile enclosure 12 of the first embodiment. As shown, the laptop computer 60 includes a laptop computer screen 62 which, when in the unfolded position, is exposed for viewing. A communications cable 64 may attach to the laptop computer 60. Sterile enclosure 12a comprises a flexible body 13a which is substantially transparent so that a surgeon may view both the keyboard and controls of the laptop computer 60 and the laptop computer screen 62. When inserted into the sterile enclosure 12a, the keyboard of the laptop computer 60 lies adjacent the closed distal end 14a of the sterile enclosure 12a. The open proximal end 16a of the sterile enclosure 12a may be appropriately sealed from the surrounding environment by rolling the distal end and then securing it to the flexible body 13a by means of tape or adhesive 18a. Cable drape 22a extends away from the sterile enclosure 12a and completely encapsulates the cable 64 therein. As with the first embodiment shown in FIG. 2, a vacuum port 24a and vacuum line 26a are provided to hold the sterile enclosure 12a tightly against the laptop computer 60.

Although the third embodiment illustrates the use of sterile enclosure 12a, the sterile enclosure 12', illustrated in FIG. 3, may be equally well suited for housing the laptop computer 60.

Figures 8, 9:
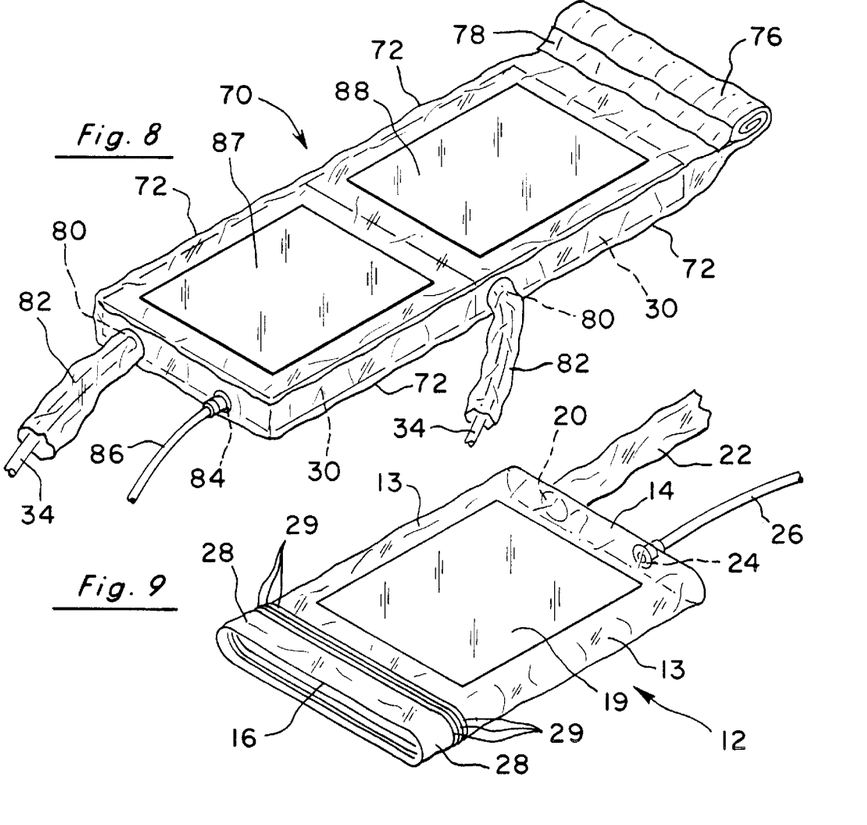
FIG. 8 is a perspective view of a fourth embodiment of the sterile encapsulated endoscopic video monitor of this invention showing two independent monitor modules encapsulated within the sterile enclosure which includes a pair of transparent covers defining corresponding window portions.
FIG. 9 is a perspective view of a sterile enclosure prior to inserting a monitor module therein.

Yet another embodiment, as shown in FIG. 8, is provided wherein a pair of side-by-side video monitors or monitor modules 30 may be placed within a single sterile enclosure 70. In some surgical procedures, it may be necessary to operate on the patient at two remote locations within the patient's body. Accordingly, it may be necessary to simultaneously view the two surgical sites. Also, it may be required to have two different views of the same surgical site which can be accommodated by viewing two monitor modules communicating with respective endoscope and camera setups. More particularly, sterile enclosure 70 includes a flexible body 72 bounded by a closed distal end 74 and open proximal end 76 which is sealed as by rolling it and sealing it to the flexible body 72 as by tape or adhesive 78. A single cable port 80 can accommodate any cables 34 from the pair of monitor modules encapsulated within the sterile enclosure 70. Accordingly, cable drape 82 attaches to flexible body 72 and covers the cable(s) 34 an appropriate length. Alternatively, as shown, a separate cable port 80 and drape 82 may be provided for each of the cables 34 of the monitor modules 30. A vacuum port 84 may be formed on the flexible body 72 in order that vacuum line 86 can communicate with a source of vacuum (not shown) so that a vacuum may be drawn on interior open space within the sterile enclosure 70. A first window portion 87 is aligned with the monitor screen of one of the monitor modules encapsulated within the sterile enclosure 70 and a second window portion 88 aligns with the other monitor module screen.

FIG. 9 illustrates the sterile enclosure 12 as packaged prior to use. As illustrated, the sterile enclosure 12 comes configured such that the open proximal end 16 includes a cuff portion 28 comprising a plurality of accordion folds 29. In order to ensure that sterility is maintained while inserting an unsterile monitor module within the sterile enclosure 12, a sterile nurse will position his/her hands between the flexible body 13 and the first fold of accordion folds 29. Then another nurse will place the monitor module within the sterile enclosure 12 by first routing any monitor module cables 34 through the cable port 20 and into the cable drape 22, and then continue to move the monitor module 30 so that it is entirely encapsulated within the sterile enclosure 12. Next, the sterile nurse will unfold the accordion folds 29 located at the open proximal end 16 of the sterile enclosure 12 and will roll fold the open proximal end 16 in order to isolate the monitor module from the outside environment. An appropriate tape or adhesive 18 may be placed over the rolled distal end of the sterile enclosure 12 providing an enclosure seal.

Figure 10:
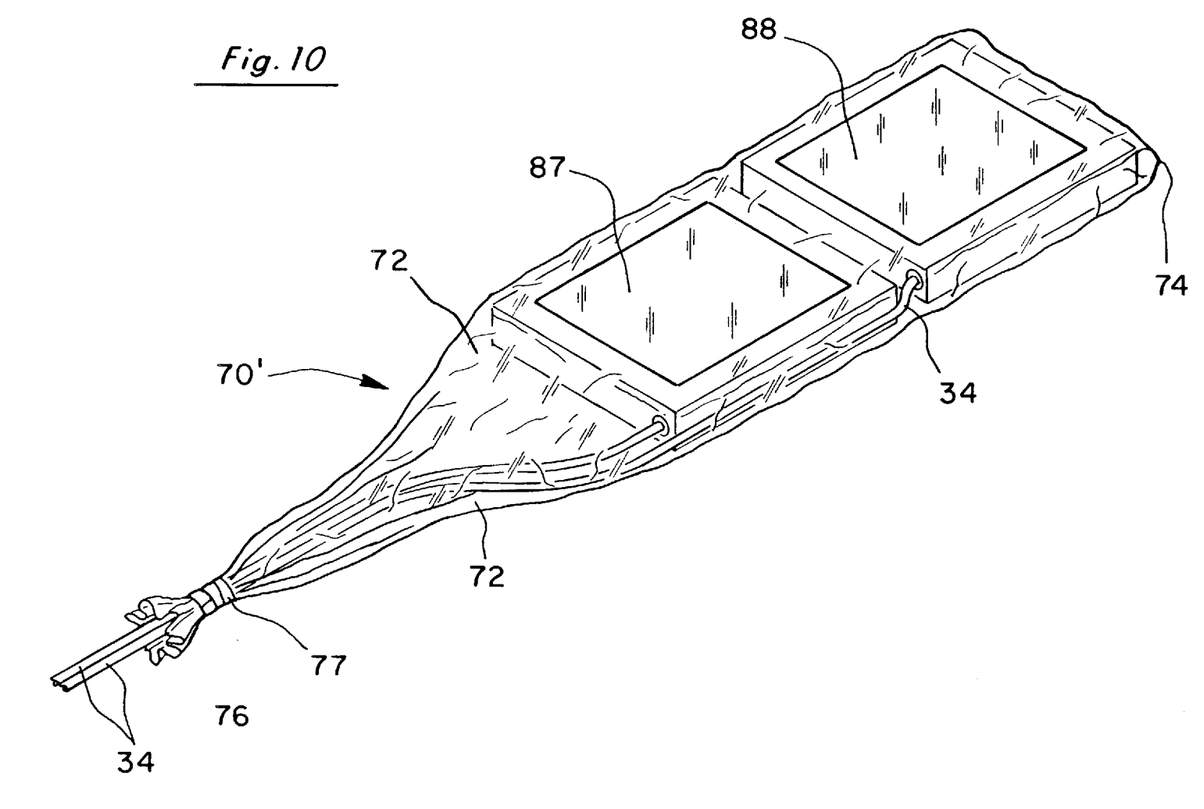
FIG. 10 is a perspective view of the fourth embodiment of the sterile encapsulated endoscopic video monitor of this invention showing two independent monitor modules encapsulated within a modified sterile enclosure which includes a pair of transparent covers defining corresponding window portions.

FIG. 10 illustrates a modified sterile enclosure 70' similar to the modified sterile 12' illustrated in FIG. 3. Modified sterile enclosure 70' eliminates the need for separate cable drapes 82 by allowing the cables 34 to simply exit through the open proximal end 76 of the sterile enclosure. As shown, a tie or an adhesive tape 77 may be provided to encapsulate the side-by-side monitor modules within the modified sterile enclosure 70'.

Figure 11:
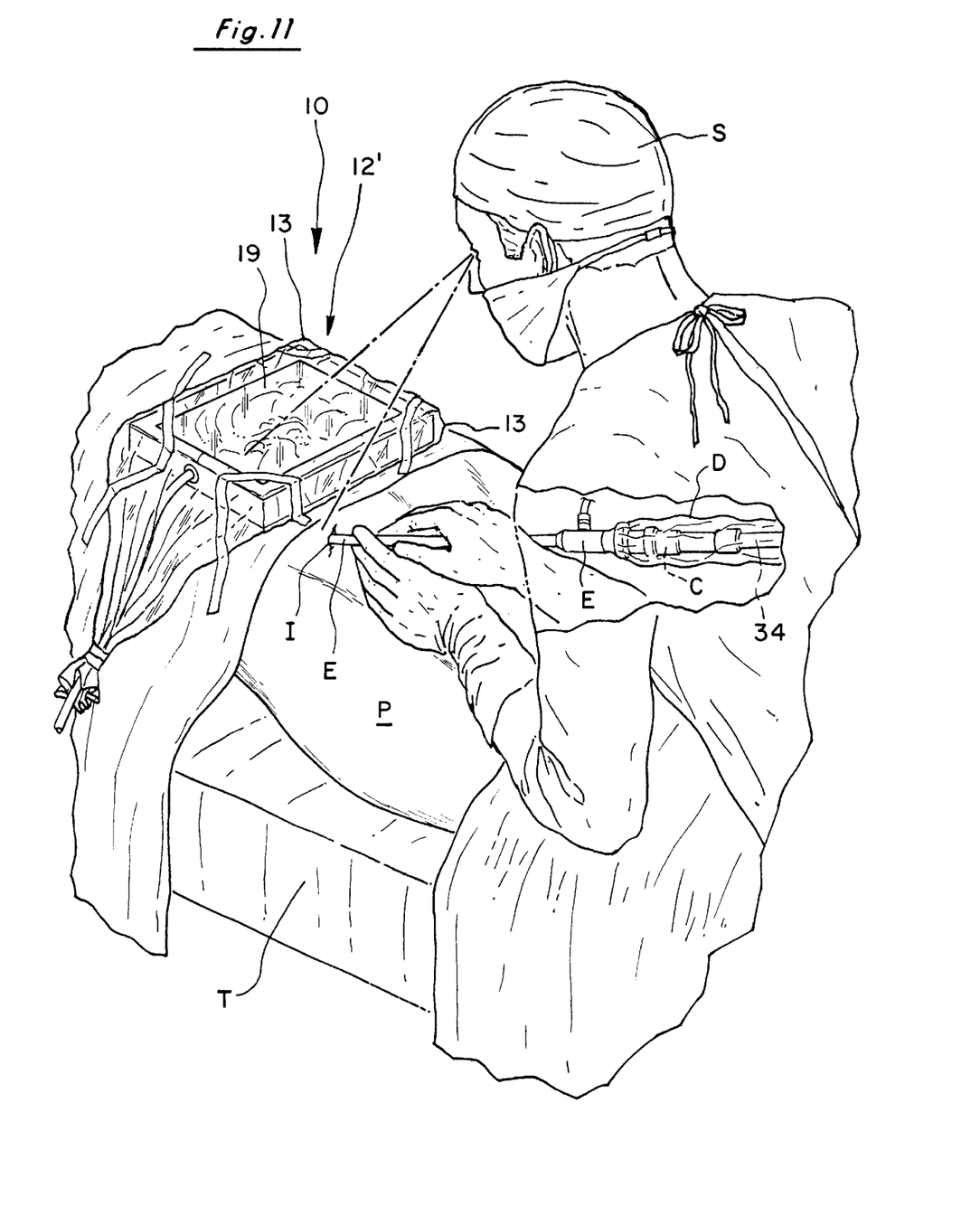
FIG. 11 is a perspective view of the sterile encapsulated endoscopic video monitor of this invention as it is being used in a surgical procedure.

As shown in FIG. 11, once the video monitor is encapsulated within a sterile enclosure, the video monitor may be placed on or adjacent to a patient P as by adhesive tape A or an appropriate support structure (not shown) in a visually aligned position with respect to the surgeon's line of vision and the surgical area(s) or site(s). A drape D is placed over the proximal end of the endoscope and over the video camera C which connects to the endoscope E. Video signals are sent directly to the video monitor via monitor cable 34. In the surgical procedure being conducted, the surgeon S is standing toward the foot of the operating table T and observes the video monitor 10 in a visually aligned position with respect to the endoscope E which is inserted into the incision I. Because of the proximity of the video monitor 10 with respect to both the surgeon S and the surgical site, the surgeon may manipulate the image produced on the video monitor 10 without having to turn away from the surgical site or by having another surgical area person adjust the image for the surgeon. The sterile field is properly protected from contamination by use of the sterile enclosure 12' which is placed over the monitor module 30.

FIGS. 12 and 13 show yet another preferred embodiment of this invention wherein the video monitors may be directly attached to an endoscopic instrument in order to provide a surgeon an aligned view of the surgical area. The monitor modules 150 in FIGS. 12 and 13 are of the type previously illustrated in FIGS. 4–6; however, the monitor modules may be of a much smaller size. Monitor modules are available from various manufacturers which can be made smaller than one square inch. Epson is one example of a manufacturer which may provide such a miniaturized monitor module. FIG. 13 illustrates the miniaturized monitor module 150 housed within a frame 140 and sealed by sealing material 159. The monitor screen 154 is covered directly by sealing material 159. FIGS. 12 and 13 show views of such a miniaturized monitor module in conjunction with an endoscopic setup as disclosed in my previous U.S. Pat. No. 5,402,768. According to such an endoscopic setup illustrated in FIG. 12, an endoscope 100 may be provided with an optical fitting 102 for communication with a light source (not shown). The endoscope 100 may couple with a connector assembly 104 which includes a light fiber connection housing 106 and a camera/endoscope coupling 108. The light fiber housing 106 enables light transmitted from a light source (not shown) and through a light-canying fiberoptic cable 112 to be transferred through to the optical fitting 102. Fiberoptic channels (not shown) within the endoscope 100 communicate with fitting 102 and extend to the distal end of the endoscope 100 (not shown) for illumination of a desired surgical area. A miniaturized endoscopic camera 110 engages the opposite end of the coupling 108 for communication with the optics of the endoscope 100 which itself is engaged with the opposite end of the coupling 108. Accordingly, an image of the surgical area as transmitted by the optics of the endoscope may be received upon the imagery of the camera 110 for creation of an image on the monitor module 150. A sterile drape 114 is provided to shield the unsterile video camera from the sterile environment of the surgical area. The image produced by the camera 110 may be produced on the monitor module without the use of connecting cables or the like. As mentioned above, some manufacturers make monitor modules which require no communication or power cables and communicate with a video camera setup by means of infrared, radio, or other electromagnetic signals. Although FIGS. 12 and 13 illustrate the miniaturized monitor module lacking any exiting communication or power cables, it will be understood by those skilled in the art that monitor modules shown in FIGS. 12 and 13 may alternatively be equipped with appropriate miniaturized cable connections for communication with a video camera system. As with the embodiment shown in FIG. 4, the miniaturized monitor modules of FIGS. 12–16 can also be equipped for control by a voice activation system. Accordingly, the microphone and speaker may be mounted adjacent the miniature monitor module or may be incorporated in a monitor module frame (not shown) which may surround the miniaturized monitor module.

The monitor modules of FIGS. 12 and 13 may be attached to the endoscope 100 by means of a monitor module mount 120 positioned on the body portion 101 of the endoscope 100. The monitor module mount 120 may take the form of two perpendicularly arranged mounts 122 and 124 as illustrated. Conveniently, the lower edge of monitor module frame 140 may be adapted to be positioned over the monitor module mount 120 for a secure engagement thereto. Mount 124 may further include one or more connectors or receptacles 126 and 128, which are adapted to mate with corresponding connectors or receptacles (not shown) on the lower rear side of the monitor module 150. These connectors or receptacles on the monitor module could serve as the link by which power and/or video signals are transmitted to the monitor module from the video control system. That is, the connectors or receptacles on the rear side of the monitor screen mate with the connectors 126 and 128. These connectors may then carry the appropriate signal through corresponding cables or wires (not shown) which may traverse through the interior of body portion 101, and ultimately connect to the camera 110 through coupling 108. In one alternative, the appropriate cables or wires (not shown) may terminate at connectors 126 and 128 and traverse through optical fitting 102 and then back to the video control system through coupling 108 and cable 112. Those skilled in the art can envision other methods by which the monitor module may be attached to the endoscope 100 as well as other methods by which the monitor module 150 can communicate with the corresponding video control system. For example, the monitor module 150 or monitor module frame 140 may include a series of locking tabs or other similar structures which securely mount the monitor module to the endoscope 100. Communication cables exiting from the monitor module may simply be placed exteriorly of the endoscope 100 and can be routed through coupling 108 and back to camera 110 or the video control system. If the visual data illustrated on the monitor screen does not need to be recorded or otherwise be manipulated by the video control system, then the video output signals from the camera may be sent directly to the monitor module via the desired cable/wire. If such data recordation or manipulation is required, then the video signal from the camera may need to first go through the video control system and then to the monitor module. As discussed above, a wireless system could be used to communicate with the monitor module in either circumstance.

As shown in FIG. 14, in lieu of monitor module 150, a miniature LCD unit may be mounted to the endoscope 100. This miniature LCD unit may be permanently attached to the endoscope and, therefore, be sterilized with the endoscope as a single unit. As shown, the miniature LCD unit 500 may include a frame portion 502 which surrounds a viewing portion 504. The use of a miniature LCD unit is further explained below with reference to FIGS. 17–19.

Figures 15, 16:
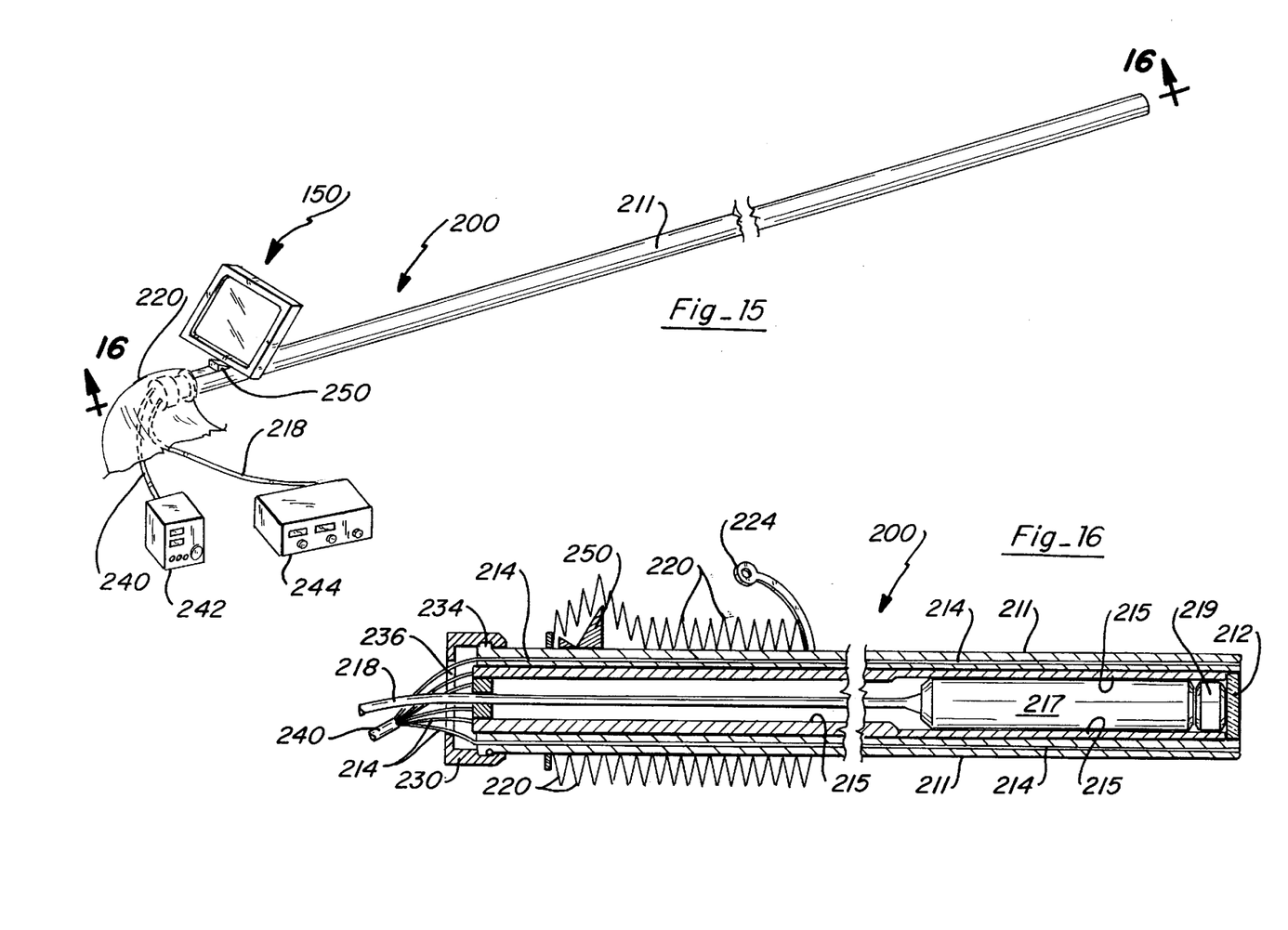
FIG. 15 is a perspective view of a monitor module mounted directly to an endoscope of the type described in my earlier U.S. Pat. No. 5,402,768.
FIG. 16 is an enlarged fragmentary vertical section, taken along line 15—15 of FIG. 15 illustrating the mounting structure for receiving the monitor module.

As illustrated in FIGS. 15 and 16, a miniaturized monitor module of this invention may also be used with an endoscopic setup as illustrated in my earlier U.S. Pat. No. 5,402,768. As shown, the endoscopic setup includes an endoscope 200 having an elongate barrel-like configuration. The endoscope includes a sterile outer sheath 211 which houses a core portion 215. The distal end of the sheath 211 includes a sealed window 212. A plurality of peripherally spaced longitudinal channels are provided in the side wall of sheath 211 for receiving light fibers 214 therethrough. The core portion 215 is removable and slidably received within the sheath 211. A housing 217 is inserted within core portion 215. An image sensor, such as a CCD or CMOS type, and its associated electronic elements (not shown) may be fixedly mounted within the housing 217. Optionally, an objective lens 219 is positionable in the distal end of core portion 215. An electronic cable 218 is provided for transmitting the electronic signals generated by the image sensor to a video control unit 244 or the like. An end cap 230 may include a pair of slots which align with and engage a plurality of spaced tabs 234 on the proximal end of sheath 211 for attaching the core portion 215 in position to with sheath 211. An opening 236 may be formed through the end cap 230 enabling structures such as cable 218 to exit therefrom. Conveniently, the light fibers 214 may be consolidated within a single cable 240 as they exit end cap 230. Cable 240 may communicate with a light source 242. In order to mount a miniaturized monitor module of this invention to the endoscope illustrated in FIGS. 15 and 16, a monitor mount 250 may be attached directly to the sheath 211. As illustrated in FIG. 16, the monitor mount 250 is covered by the sterile drape 220 prior to the endoscope being placed in operation. When it is desired to place the endoscope in operation, a pull tab 224 of the sterile drape 220 is pulled in a proximal direction thus causing the sterile drape to cover the trailing cables 218 and 240. As the sterile drape 220 is pulled in the proximal direction, the monitor mount 250 is exposed and which may then receive the miniaturized monitor module 150. The miniaturized monitor module in FIGS. 15 and 16 may be attached to the monitor mount 250 as previously described with respect to FIGS. 12 and 13. As with the embodiment shown in FIGS. 12 and 13, a video control unit may communicate with the miniaturized monitor module for producing an image thereon via desired electromagnetic means. Alternatively, connections located on the rear side of the monitor module and on the mount 250 may be utilized to allow a camera control unit to communicate with the miniaturized monitor module. The image produced on the miniaturized monitor module may be controlled either from the remote video control unit, directly on the monitor module itself via touch screen switches, or voice activation as described previously in reference to the monitor modules illustrated in FIGS. 1–6.

Figure 17:
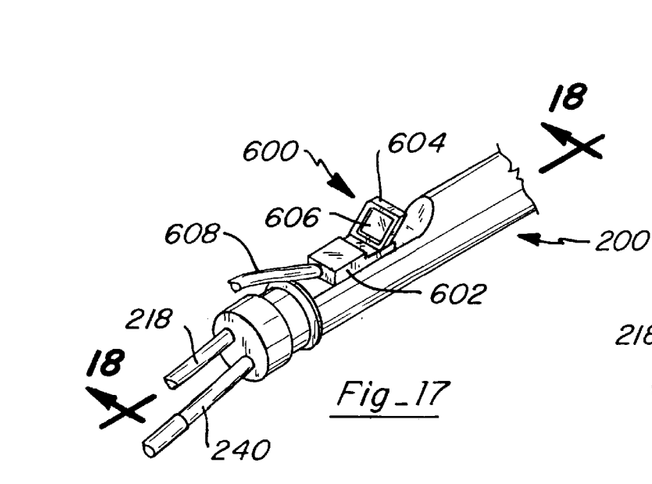
FIG. 17 is a fragmentary perspective view of the endoscope shown in FIG. 14, said endoscope including an integral LCD display unit in lieu of a monitor module.

FIG. 17 illustrates the endoscope of FIGS. 15 and 16 incorporating the use of a miniature LCD unit 600. As shown, the LCD unit attaches to the endoscope 200 by means of mount 602. The LCD unit includes a frame portion 604 which surrounds the viewing portion 606.

Figure 18:
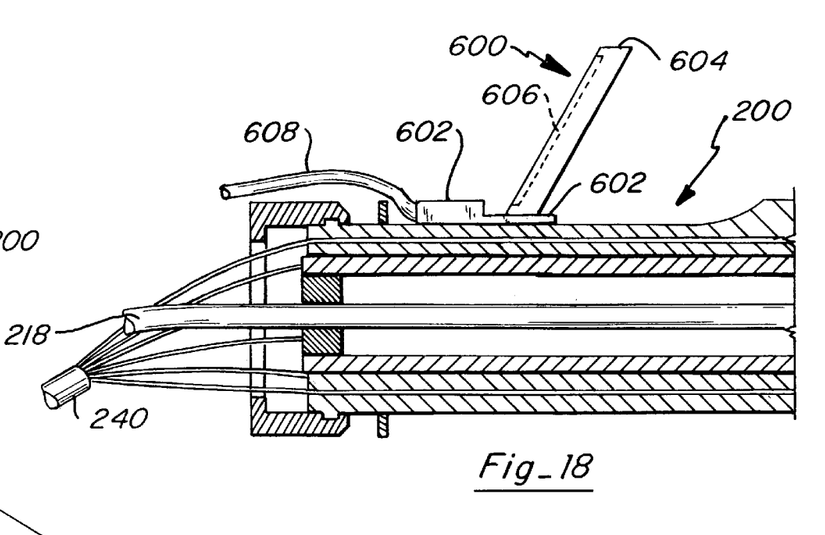
FIG. 18 is an enlarged fragmentary vertical section, taken along line 18—18 of FIG. 17 illustrating the LCD display unit mounted directly to the sheath or outer surface of the endoscope.

FIG. 18 illustrates one manner in which the LCD unit 600 may be directly mounted to the endoscope 200. As shown, the LCD unit is mounted directly to the sheath 211 and cable 608 extends proximally with cables 218 and 240. Cable 608 communicates with the video camera system for receiving those video signals so that an image of the surgical area may be viewed on viewing portion 606. Mount 602 may be attached to the endoscope 200 so that a watertight connection is achieved. Furthermore, the LCD unit 600 and mount 602 may be coated with an appropriate material such as acrylic or the like which enables the LCD unit to be sterilized along with the endoscope as a single unit. The LCD unit may be removed from the sheath 211 after use as the sheath is considered a disposable element and is riot intended to be used again.

Figure 19:
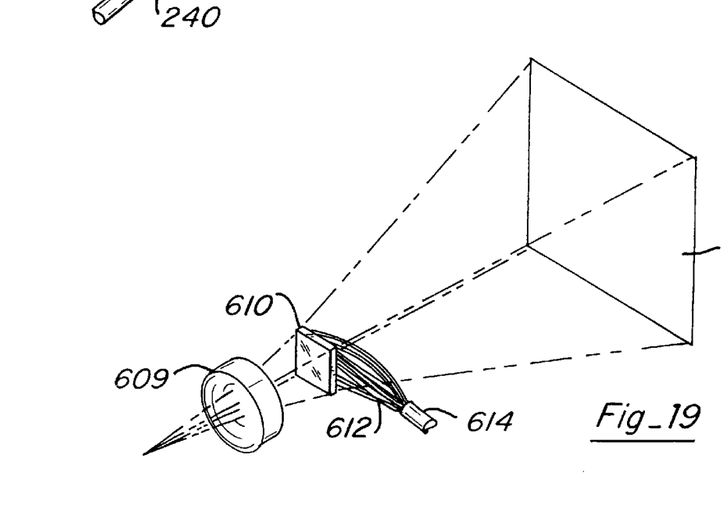
FIG. 19 is a schematic diagram illustrating the use of a LCD display unit in producing an enlarged virtual image.

FIG. 19 is a schematic diagram showing an enlarged virtual image 620 which is perceived by a surgeon who looks through a lens 609 onto the AMLCD element 610. The lens 609 can be 1 inch square or smaller. The eyes of the surgeon are directed onto the element 610 which produces the greatly enlarged virtual image 620. The AMLCD element 610 communicates with the video camera system by means of transmission wires or connectors 612 which may be housed by cable 614. Cable 614 may then connect to cable 608 in order to link the LCD unit with the video camera system. Depending upon the imaging system used in the endoscope, it is possible to transmit imaging signals received by the endoscope directly to the LCD unit. That is, it may be unnecessary to transmit imaging signals to a video camera system before sending such signals to the LCD unit. The virtual image may appear as large as 20 inches at a virtual distance of five feet. In other words, the image presented to the eye replicates a much larger visual display by use of the active matrix liquid crystal display-type device. Typically, a surgeon must place the eye within three to five inches of the viewing portion 606 to see the enlarged virtual image. As mentioned above, Kopin Corporation manufactures a product known as the Cyber Display 320 which can produce the enlarged virtual display 620. Thus, a surgeon can view the desired surgical area by use of a very small LCD display unit which directly attaches to the endoscope in an aligned position with respect to the surgical area.

Figure 20:
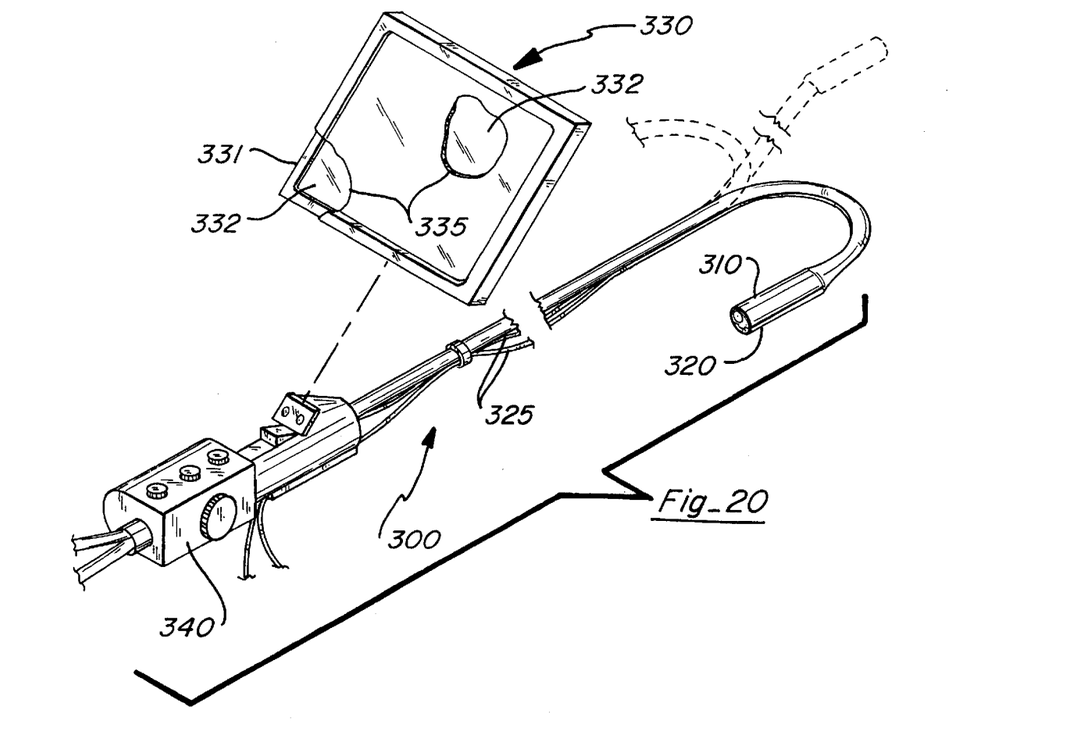
FIG. 20 is a perspective view of a monitor module mounted directly to an endoscope of the type described in my earlier U.S. Pat. No. 5,489,256.

FIG. 20 illustrates yet another endoscopic setup which may utilize a miniaturized monitor module. This endoscope is fully described in my earlier U.S. Pat. No. 5,489,256. As shown, the endoscopic setup includes a flexible and steerable endoscope 300 comprising a capsule portion 310 and a separable disposable tube or channel section 320. Channel section 320 may have a plurality of tubes 325 which communicate with a source of fluid, vacuum, or may carry therethrough an appropriate operative instrument (not shown). The monitor module 330 is mounted to a proximal end of the endoscope 300 and adjacent to control assembly 340 which may manipulate the flexible endoscope within the body. The monitor module 330 may be mounted to the endoscope 300 by the methods previously described with respect to FIGS. 12, 13, 15 and 16. The monitor module 330 may include a screen portion 332 housed within frame 331 and completely sealed by sealing material 335. As with the previous embodiments, the features of the monitor module may be controlled via a wired or wireless system, or by voice activation.

Figure 21:
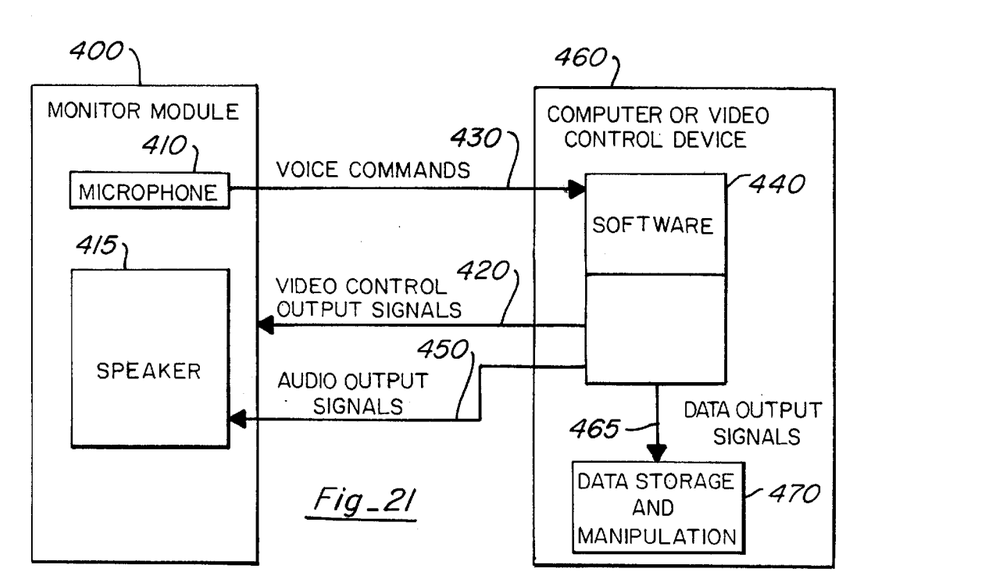
FIG. 21 is a schematic diagram illustrating one method by which a voice activated system may be used to control the functions of a video monitor.

In order to better understand the voice activation system and how it is able to control the monitor module, FIG. 21 illustrates a schematic diagram of a voice activation system. The monitor module 400 may have located thereon a microphone 410 and a speaker 415. The microphone provides voice command input signals 430 to computer software 440 which interprets and translates the voice signal as a specific functioning command. The computer software then causes appropriate output signals 420 to be sent to the monitor module which control the video functions of the monitor module. Additionally, the software may create audio output signals 450 to speaker 415 so the surgeon may hear certain status or alarm signals. The computer software 440 may be run by a standard personal computer 460, or may be run by a video control unit having a microprocessor and other needed hardware. Also, the computer software may not only control the functioning of the monitor module, but may also be used to store and manipulate data as desired by the surgeon. Accordingly, the software 440 can cause output signal 465 to send the desired data to a storage device or printer 470. As mentioned previously, the Endoview™ and Endospeak® products are video documentation systems that enable the surgeon to have voice activated control of a video monitor and to retain and use the video data in the desired format.

By providing a miniaturized monitor module or LCD display unit and directly attaching it to an endoscopic setup, a surgeon is provided a means by which to view the surgical area in almost a perfectly aligned orientation. In other words, the use of a miniaturized monitor module or LCD display unit attached directly to the endoscope more directly simulates the distal end of the endoscope being exposed for observation by the surgeon. Because the monitor module is of such a small size and weight, the addition of the monitor module or LCD display unit to the endoscopic setup does not materially affect the surgeon's ability to manipulate the endoscopic instrument. Although the monitor module or LCD display unit may be less than 1 inch square, it can be increased in size to accommodate a clear view of the surgical area, yet still be small enough to not materially affect the surgeon's ability to manipulate the endoscopic instrument. Furthermore, since both the miniaturized monitor module and LCD display unit can be made completely sterile, they can be introduced into the sterile field of the surgical area and adjusted on the endoscopic instrument as desired.

In accordance with the invention and method described above, numerous problems associated with the use of video equipment in endoscopic procedures can be overcome. Since the sterile encapsulated endoscopic video monitor provides a means by which a surgeon may conveniently position a video image of the surgical site in visual alignment with the surgical area, the surgeon's ability to properly manipulate an endoscope is greatly enhanced. Also, surgeon fatigue will be minimized by preventing the surgeon from conducting a surgical procedure in a strained position. That is, since the surgeon does not have to look away from the surgical area to view the monitor module, the surgeon may be in a more natural position.

Since the monitor module contained within the sterile enclosure is small and lightweight, and also may include integral switches for controlling the type of image viewed, the surgeon may easily adjust the type of image to be viewed as well as position the monitor module with a minimum amount of disruption during a surgical procedure. Alternatively, the surgeon may simply control functioning of the monitor module by voice commands. By the use of the sterile enclosure which completely encloses the monitor module and any associated cables, the encapsulated video monitor may be placed within the sterile field of the surgical area; however, sterility is not sacrificed at the cost of achieving improved imaging of the surgical area.

If the surgeon is required to make an additional incision and operate on the patient at another surgical area, the encapsulated endoscopic video monitor may be easily moved to a new location and be visually aligned.

This invention has been described in detail with reference to particular embodiments thereof, but it will be understood that various other modifications can be effected within the spirit and scope of this invention.

What is claimed is:

1. In combination, an endoscope and an apparatus for viewing a surgical area, said combination comprising:
   an endoscope including proximal and distal ends;
   a video monitor mounted to said proximal end of said endoscope and having a viewing screen enabling a surgeon to view the surgical site as imaged by said endoscope; and
   a sterile enclosure made of substantially liquid and gas impervious material for encapsulating said video monitor therein, said sterile enclosure being transparent at least in an area where said viewing screen is located.

2. A combination, as claimed in claim 1, further including:
   at least one waterproof cable including a waterproof connector attached to an end thereof, said connector being engageable with said sterile enclosure forming a waterproof connection therebetween.

3. A combination, as claimed in claim 1, further including:
   a cable drape connected to said sterile enclosure.

4. A combination, as claimed in claim 1, wherein said sterile enclosure includes:
   a frame enclosing and sealing said video monitor therein, said frame including a transparent cover positioned over said viewing screen of said video monitor.

5. A combination, as claimed in claim 1, wherein said sterile enclosure includes:
   a flexible body having a transparent portion which is alignable with said viewing screen of said video monitor.

6. A combination, as claimed in claim 1, wherein said sterile enclosure includes:
   a sealing material for encapsulating said video monitor therein.

7. A combination, as claimed in claim 1, wherein said sterile enclosure further includes:
   a window portion sealed to an opening formed in said sterile enclosure, said window portion being aligned with said viewing screen of said video monitor.

8. A combination, as claimed in claim 1, further including:
   a mount secured to said proximal end of said endoscope for serving the means by which said video monitor mounts to said endoscope; and
   said endoscope extends along a longitudinal axis and said mount extends away from said axis at a desired angle such that when said video monitor is mounted on said mount to said endoscope, said viewing screen also extends away from said axis along said angle enabling the surgeon to view said video monitor along a line of sight which matches said angle.

9. A method of performing an endoscopic procedure in the sterile field of a surgical area, said method comprising the steps of:
   providing a first endoscopic instrument to be used in the procedure;
   providing a first video camera communicating with the first endoscopic instrument for capturing visual images of the surgical area;
   attaching a first video monitor to the first endoscopic instrument in an aligned position with respect to a surgeon's desired line of sight to the surgical area;
   placing the first video monitor attached to the first endoscopic instrument in the sterile field of the operating area; and
   performing the endoscopic procedure with the first endoscopic instrument while the first video monitor is attached to the first endoscopic instrument and provides the visual images of the surgical area.

10. A method, as claimed in claim 9, further including the step of:
    controlling images of the surgical area as viewed on the first video monitor by manipulation from a remote location.

11. A method, as claimed in claim 9, further including the steps of:
    removing the first video monitor attached to the first endoscopic instrument; and
    replacing the first video monitor with a second video monitor and attaching the second video monitor on the first endoscopic instrument for providing an enhanced image of the surgical area.

12. A method, as claimed in claim 9, further including the steps of:
    removing the first video monitor attached to the first endoscopic instrument;

introducing a second endoscopic instrument into the surgical area; and attaching the first video monitor to the second endoscopic instrument.

13. A method, as claimed in claim 9, further including the step of:

controlling images of the surgical area as viewed on the first video monitor by controls located on the first video monitor.

14. A method, as claimed in claim 9, further including the steps of:

providing a second endoscopic instrument to be used in the procedure;

attaching a second video monitor to the second endoscopic instrument in an aligned position with respect to the surgeon's desired line of sight to the surgical area; and performing the endoscopic procedure with the first and second endoscopic instruments while the first video monitor is attached to the first endoscopic instrument and the second video monitor is attached to the second endoscopic instrument.

15. A method, as claimed in claim 9, further including the step of:

controlling images of the surgical area as viewed on the first video monitor by remote control.

16. A method, as claimed in claim 15, wherein:

said remote control is achieved by voice activation.

17. A method, as claimed in claim 9 wherein:

said video monitor is a monitor module.

18. A method, as claimed in claim 9, wherein:

said video monitor is a LCD display unit.

\* \* \* \* \*